(12) United States Patent
Yuan et al.

(10) Patent No.: US 12,138,129 B2
(45) Date of Patent: Nov. 12, 2024

(54) IMAGING SYSTEM FOR SURGICAL ROBOT, AND SURGICAL ROBOT

(71) Applicant: SHANGHAI MICROPORT MEDBOT (GROUP) CO., LTD., Shanghai (CN)

(72) Inventors: Shuai Yuan, Shanghai (CN); Yunlei Shi, Shanghai (CN); Jiayin Wang, Shanghai (CN); Chao He, Shanghai (CN)

(73) Assignee: SHANGHAI MICROPORT MEDBOT (GROUP) CO., LTD., Shanghai (CN)

( * ) Notice: Subject to any disclaimer, the term of this patent is extended or adjusted under 35 U.S.C. 154(b) by 674 days.

(21) Appl. No.: 17/423,026

(22) PCT Filed: Jan. 13, 2020

(86) PCT No.: PCT/CN2020/071829
§ 371 (c)(1),
(2) Date: Jul. 14, 2021

(87) PCT Pub. No.: WO2020/147691
PCT Pub. Date: Jul. 23, 2020

(65) Prior Publication Data
US 2022/0079706 A1  Mar. 17, 2022

(30) Foreign Application Priority Data
Jan. 14, 2019  (CN) .......................... 201910032829.2

(51) Int. Cl.
*A61B 90/00* (2016.01)
*A61B 1/00* (2006.01)
(Continued)

(52) U.S. Cl.
CPC .............. *A61B 90/37* (2016.02); *A61B 34/37* (2016.02); *A61B 1/00048* (2013.01);
(Continued)

(58) Field of Classification Search
CPC ..... A61B 90/37; A61B 34/37; A61B 1/00048; A61B 2034/2048; A61B 2034/2051;
(Continued)

(56) References Cited

U.S. PATENT DOCUMENTS

| | | | |
|---|---|---|---|
| 9,645,785 B1 | 5/2017 | Hannaford | |
| 2004/0047044 A1* | 3/2004 | Dalton | A61B 6/5247 359/630 |

(Continued)

FOREIGN PATENT DOCUMENTS

| | | |
|---|---|---|
| CN | 102186434 A | 9/2011 |
| CN | 104135962 A | 11/2014 |

(Continued)

*Primary Examiner* — Abby Y Lin
*Assistant Examiner* — Esvinder Singh
(74) *Attorney, Agent, or Firm* — MUNCY, GEISSLER, OLDS & LOWE, P.C.

(57) ABSTRACT

An imaging system for a surgical robot and a surgical robot. The imaging system includes: a fixed display device for acquiring and displaying image information about a surgical environment; a movable display device, which is coupled, so as to be movable relative, to the fixed display device, the movable display device configured to acquire and display the same image information as is displayed by the fixed display device; and a console having a support on which the fixed display device is mounted. The combined use of the movable display device with the fixed display device in the imaging system and the surgical robot provide more options of operation to an operator. The movable display device can be adjusted according to the desired comfort and personal preferences of the operator to provide the operator with an (Continued)

experience of increased operational comfort and reduce the fatigue of the operator.

13 Claims, 5 Drawing Sheets

(51) Int. Cl.
  *A61B 34/20* (2016.01)
  *A61B 34/37* (2016.01)
(52) U.S. Cl.
  CPC .............. *A61B 2034/2048* (2016.02); *A61B 2034/2051* (2016.02); *A61B 2090/3614* (2016.02); *A61B 2090/372* (2016.02)
(58) Field of Classification Search
  CPC ...... A61B 2090/3614; A61B 2090/372; A61B 1/00045; A61B 5/7445; A61B 6/462; A61B 6/464; A61B 8/464; A61B 8/462; A61B 2017/00199; A61B 17/1626; A61B 1/00009; A61B 1/0052; A61B 2034/301; A61B 34/30; A61B 34/00; A61B 34/20; A61B 34/25; A61B 34/70; A61B 1/000095; A61B 90/361
  See application file for complete search history.

(56) References Cited

U.S. PATENT DOCUMENTS

| | | | |
|---|---|---|---|
| 2007/0156285 A1* | 7/2007 | Sillman | A61B 34/70 700/251 |
| 2013/0197364 A1* | 8/2013 | Han | A61B 8/14 600/440 |
| 2016/0120507 A1* | 5/2016 | Ninomiya | G06F 3/1431 361/679.04 |
| 2016/0220324 A1 | 8/2016 | Tesar | |
| 2017/0007351 A1 | 1/2017 | Yu | |
| 2017/0057086 A1* | 3/2017 | Hida | B25J 9/1664 |
| 2017/0143442 A1 | 5/2017 | Tesar et al. | |
| 2018/0078316 A1 | 3/2018 | Schaewe | |
| 2018/0092706 A1 | 4/2018 | Anderson et al. | |
| 2018/0296174 A1* | 10/2018 | Barker | A61B 6/4441 |
| 2018/0368656 A1* | 12/2018 | Austin | A61B 1/045 |
| 2019/0132801 A1* | 5/2019 | Kamath | G16H 40/63 |

FOREIGN PATENT DOCUMENTS

| | | |
|---|---|---|
| CN | 106456145 A | 2/2017 |
| CN | 107028662 A | 8/2017 |
| CN | 108289600 A | 7/2018 |
| CN | 108701429 A | 10/2018 |
| CN | 109806002 A | 5/2019 |
| RU | 2594100 C1 | 8/2016 |
| WO | WO2009051013 A1 | 4/2009 |

\* cited by examiner

IMAGING SYSTEM FOR SURGICAL ROBOT, AND SURGICAL ROBOT

TECHNICAL FIELD

The present invention relates to the field of medical instruments and, more specifically, to an imaging system for a surgical robot, and to a surgical robot.

BACKGROUND

The advent of surgical robots is in line with the trend of development toward precision surgery, and surgical robots can be used as powerful helping tools for surgeons. For example, Da Vinci surgical robots have been deployed in many large hospitals around the world to provide patients with a wide range of benefits including minimal trauma, less bleeding and fast recovery.

In the medical field, surgical robots are designed to perform complex surgical procedures in a minimally invasive manner. Using surgical robots in place of traditional surgical instruments can tackle various challenges with the traditional surgery, because they can break through the limitations of the human eye by more clearly displaying internal organs to the operator using stereoscopic imaging technology. Robotic arms can perform 360-degree pivoting, shifting, swinging, pinching and other complicated actions that are difficult for human to perform even in areas inaccessible for human hands, and avoid the problem of trembling. Surgical robots have gained extensive popularity among both surgeons and patients and found extensive use in various clinical surgical procedures thanks to their advantages including minimal trauma, less bleeding, fast recovery, greatly shortened postoperative hospital stay and significantly improved postoperative survival and recovery.

In the current surgical practice, a lack of convenience has been found in the sole reliance on a stereoscopic imaging device equipped in the surgeon's console, because the fixed arrangement of the imaging system in the console reduces its flexibility and interactability with the patient's body, and may lead to tiredness and fatigue over time. In order to overcome this, there are some imaging systems additionally equipped with a portable, compact head-mounted display device, which can be used flexibly to relieve the surgeon's fatigue resulting from manipulating the surgical robot, because he/she is exempted from having to keep a sitting position for a long time. Moreover, stereoscopic endoscopic images collected during surgery can be simultaneously and synchronously transmitted to both the surgeon's console and the head-mounted display device. However, such head-mounted display devices could still exhibit some inconveniences, such as inconvenient removal, and having to take off the helmet when needing to visually check something else during the procedure.

A Chinese patent application published as CN102186434A discloses a three-dimensional (3D) display system for a surgical robot and a method for controlling the system. The main idea of this prior disclosure is to cause a 3D display device to move with an operator during a robotic surgical procedure so as to allow the operator to perform the procedure while conveniently viewing a 3D image as necessary, without a need to change his or her body position or wear a display device. Although this can alleviate fatigue of the operator to a certain extent, the whole display system occupies a large space, and there are considerable positional deviations between the robotic arm and the display, which lead to a less "immersive" experience of operation.

A Chinese patent application published as CN106456145A proposes a virtual reality surgical device including a visualization system operably connected to a central body, a head-mounted display in the visualization system, and sensors for tracking the position and/or orientation in space of the head-mounted display relative to a reference point, and thus allowing adjusting the field of view of a camera. This technique focuses on how to control the camera using the head-mounted display. However, it is associated with the problems of tiredness or fatigue occurring when the head-mounted display is worn for a long time and inconvenient removal thereof. Further, its application in imaging systems for surgical robots is limited.

Therefore, there is a need in the art for an imaging system that can mitigate the above-discussed problems and provide an operator with increased comfort and a real-time synchronized reference image, as well as for a corresponding surgical robot.

SUMMARY OF THE INVENTION

It is an objective of the present invention to provide an imaging system for a surgical robot, which can provide an operator with an experience of increased operational comfort and reduce fatigue of the operator.

It is another objective of the present invention to provide an imaging system for a surgical robot, which can be used in surgical training and education applications and ensure that an operator and spectators watch an image with the same view.

It is still another objective of the present invention to provide a surgical robot, which enables an operator to have a sense of immersion when operating a master manipulator based on the imaging system.

It is a further objective of the present invention to provide a surgical robot, which allows direct control of an image capture device with a movable display device, providing an operator with more convenient control and enhanced smoothness of surgical operations and high surgical efficiency.

To achieve the above objectives, the present invention provides an imaging system for a surgical robot, comprising:

a fixed display device configured to acquire and display image information about a surgical environment;

a movable display device, which is coupled to the fixed display device, and is movable relative to the fixed display device the movable display device configured to acquire and display the image information that is displayed by the fixed display device; and a console having a support on which the fixed display device is mounted.

Additionally, the fixed display device is movably connected to the support of the console so that the fixed display device is movable relative to the support of the console.

Additionally, the imaging system further comprises a guide track mounted on the support of the console, and a turntable structure configured to be moved rotatably and/or translationally along the guide track, wherein the fixed display device is connected to the support of the console via the turntable structure and guide track.

Additionally, the fixed display device comprises a first display element, a second display element, a first reflector group, a second reflector group, and an image viewer having a first viewing window and a second viewing window, wherein the first display element and the second display element are configured to respectively receive image signals indicative of respective images with binocular disparity therebetween and display the images, the first reflector group is configured to reflect the image displayed on the first display element to the first viewing window of the image viewer, the second reflector group is configured to reflect the image displayed on the second display element to the second viewing window of the image viewer, and each of the first viewing window and the second viewing window is configured to receive the image displayed on one of the display elements.

Additionally, the movable display device is movably connected to the image viewer of the fixed display device or on either side of the fixed display device.

Additionally, the movable display device comprises a third display element and a fourth display element, wherein each of the third display element and the fourth display element is communicatively connected to a signal source for a respective one of the display elements of the fixed display device so as to able to acquire an image signal same as the image signal received by the respective display element.

Additionally, the movable display device comprises a third display element, a fourth display element, a first light reception element, a second light reception element, a first optical fiber, a second optical fiber, a first image sensing element, a second image sensing element, a first image processing element and a second image processing element;

wherein a first catadioptric lens is mounted to the first viewing window of the image viewer in the fixed display device, and configured to allow part of light of an image displayed on the first display element, which has been reflected by the first reflector group, to pass through the first catadioptric lens onto the first viewing window and to reflect rest of the light onto the first light reception element, and the reflected part of the light is then transmitted through the first optical fiber to the first image sensing element and photoelectrically converted by the first image sensing element into an electrical signal which is received by the first image processing element, undergoes image enhancement processing therein, and the third display element is configured to display an image resulting from the image enhancement processing in the first image processing element; and wherein a second catadioptric lens is mounted to the second viewing window of the image viewer in the fixed display device, and configured to allow part of light of an image displayed on the second display element, which has been reflected by the second reflector group, to pass through the second catadioptric lens onto the second viewing window and to reflect the rest of the light onto the second light reception element, and the reflected part of the light is then transmitted through the second optical fiber to the second image sensing element and photoelectrically converted thereby into an electrical signal which is received by the second image processing element, undergoes image enhancement processing therein, and the fourth display element is configured to display an image resulting from the image enhancement processing in the second image processing element.

The present invention also provides a surgical robot comprising the above imaging system.

Additionally, the surgical robot further comprises a controller configured to determine which one of the movable display device and the fixed display device is selected as a primary display device according to a selection from an operator.

Additionally, the surgical robot further comprises an image capture device, a surgical instrument and a master manipulator on the console, wherein the image capture device comprises an endoscope configured to capture the image information about the surgical environment, the fixed display device is communicatively connected to the endoscope so as to acquire the image information about the surgical environment, wherein the master manipulator is configured to control position and orientation adjustment to the surgical instrument, wherein coordinate systems are defined respectively for the fixed display device, the movable display device and the endoscope, and wherein the controller is further configured to match a movement direction and/or an orientational change pattern of the master manipulator in the coordinate system of the primary display device with a movement direction and/or an orientational change pattern of the surgical instrument in the coordinate system of the endoscope.

Additionally, coordinate systems are defined respectively for a grip of the master manipulator and for the console; and the controller is further configured to make an orientation adjustment to the coordinate system of the grip in the coordinate system of the support of the console based on an orientation change of the coordinate system of the primary display device in the coordinate system of the support of the console, and to make an orientation adjustment to the master manipulator based on an orientation representation of the surgical instrument in the coordinate system of the endoscope so as to match an orientation representation of the master manipulator in the coordinate system of the primary display device with the orientation representation of the surgical instrument in the coordinate system of the endoscope.

Additionally, the movable display device is provided with a gyroscope configured to detect an orientation of the coordinate system of the movable display device in the coordinate system of the support of the console, and the controller is communicatively connected to the gyroscope so as to determine an orientation change of the coordinate system of the movable display device in the coordinate system of the support of the console, or wherein the movable display device is provided with a magnetic field sensor and a horizon sensor, which are configured to detect an orientation of the coordinate system of the movable display device in the coordinate system of the support of the console, and the controller is communicatively connected to both the magnetic field sensor and the horizon sensor so as to determine an orientation change of the coordinate system of the movable display device in the coordinate system of the support of the console based on a principle of electromagnetic induction.

Additionally, the fixed display device is movably mounted on the console via a turntable structure so as to be movable relative to the console, and wherein the turntable structure is provided thereon with a position sensor configured to sense an angle of rotation of the fixed display device, and the position sensor is communicatively connected to the controller so that the controller is able to determine an orientation change of the coordinate system of the fixed display device in the coordinate system of the support of the console using both the position sensor and a kinematic model.

Additionally, coordinate systems are defined respectively for a grip of the master manipulator and for the console; and when the primary display device is switched from the movable display device to the fixed display device, the controller determines a movable-to-fixed rotation matrix from an orientation of the coordinate system of the movable display device in the coordinate system of the support of the console and an orientation of the coordinate system of the fixed display device in the coordinate system of the support of the console, adjusts an orientation of the coordinate system of the grip in coordinate system of the support of the console based on the movable-to-fixed rotation matrix, and makes an orientation adjustment to the master manipulator based on the an orientation representation of the surgical instrument in the coordinate system of the endoscope so as to match an orientation representation of the master manipulator in the coordinate system of the fixed display device with the orientation representation of the surgical instrument in the coordinate system of the endoscope.

Additionally, coordinate systems are defined respectively for a grip of the master manipulator and for the console; and when the primary display device is switched from the fixed display device to the movable display device, the controller determines a fixed-to-movable rotation matrix from an orientation of the coordinate system of the movable display device in the coordinate system of the support of the console and an orientation of the coordinate system of the fixed display device in the coordinate system of the support of the console, adjusts an orientation of the coordinate system of the grip in the coordinate system of the support of the console based on the fixed-to-movable rotation matrix, and makes an orientation adjustment to the master manipulator based on the an orientation representation of the surgical instrument in the coordinate system of the endoscope so as to match an orientation representation of the master manipulator in the coordinate system of the movable display device with the orientation representation of the surgical instrument in the coordinate system of the endoscope.

Additionally, the image capture device further comprises: an actuation element configured to adjust an orientation of the endoscope, and an orientation detection element configured to detect the orientation of the endoscope, and wherein the controller is communicatively connected to both the actuation element and the orientation detection element and is configured to control the actuation element, based on an orientation of the movable display device and a current orientation of the endoscope, to drive the endoscope so as to achieve a match between the orientations of the endoscope and the movable display device.

Additionally, the image capture device further comprises an endoscope holding arm by which the endoscope is held, wherein the endoscope holding arm comprises a plurality of joints, the orientation detection element is connected to the joints to detect angles of rotation of the joints, and the actuation element is connected to the joints to drive the joints to move, and wherein the controller is configured to determine a current orientation of the endoscope from measurements of the orientation detection element using a kinematic model, determine amounts of rotation for the respective joints of the endoscope holding arm from the orientation of the movable display device, and control the actuation element to drive the joints to rotate to result in a match between the orientations of the endoscope and the movable display device.

Additionally, the image capture device further comprises a follow switch communicatively connected to the controller, wherein the follow switch is configured to enable or disable the controller to control the endoscope to vary in position or orientation with the movable display device.

Additionally, a coordinate system is defined for a grip of the master manipulator; and the controller is further configured to adjust an orientation of the coordinate system of the grip and the orientation of the endoscope based on an orientation change of the coordinate system of the movable display device in the coordinate system of the support of the console and to adjust an orientation of the master manipulator based on an orientation representation of the surgical instrument in the adjusted coordinate system of the endoscope so as to achieve a match between an orientation representation of the master manipulator in the coordinate system of the movable display device and an orientation representation of the surgical instrument in the adjusted coordinate system of the endoscope.

Compared to the prior art, the present invention provides an imaging system, which combines a movable display device with a fixed display device, providing more options of operation to an operator. The movable display device can be adjusted according to the desired comfort and personal preferences to provide the operator with an experience of increased operational comfort and reduce the fatigue of the operator.

Additionally, a plurality of the movable display devices may be included, and image information can be synchronized between the individual movable display devices and between each movable display device and the fixed display device. This enables the operator and assisting staff to watch the progress of a surgical procedure with the same view, increasing safety of the procedure. When used in surgical training and education applications, the participation of an operator and several trainees is allowed, ensuring enhanced reality of the training and improved training efficiency.

The present invention also provides a surgical robot, which incorporates the imaging system and preferably matches a movement direction and/or orientational change pattern of a master manipulator in a coordinate system of a primary display device with a movement direction and/or orientational change pattern of a surgical instrument in a coordinate system of an endoscope. The surgical robot provides an operator with an immersive experience, so as to achieve the correct motion detection and control, and higher control accuracy in performing image information based operations.

In addition, the surgical robot allows the orientation of an endoscope, a laparoscope or a similar instrument in an image capture device to change with the orientation change of the movable display device. In this way, the endoscope, laparoscope or instrument moves exactly as desired by the operator, enabling a surgical procedure to be conducted more smoothly with increased efficiency.

In these figures, 10 denotes a movable display device; 20, a fixed display device; 30, a support of console; 11, a cable; 12, a first light reception element; 12', a second light reception element; 13, a first optical fiber; 13', a second optical fiber; 21, a turntable structure; 22, an image viewer; 23, a first display element; 23', a second display element; 24, a first catadioptric lens; 24', a second catadioptric lens; 25, a virtual image; 26, a first reflector group; and 26', a second reflector group.

DETAILED DESCRIPTION

Imaging systems for a surgical robot and surgical robots proposed in accordance with particular embodiments of the present invention will be described in greater detail below with reference to the accompanying drawings. Features and advantages of the present invention will be more apparent from the following description, and from the appended claims. Note that the figures are provided in a very simplified form not necessarily drawn to exact scale for the only purpose of helping to explain the disclosed examples in a more convenient and clearer way.

Figure 1:
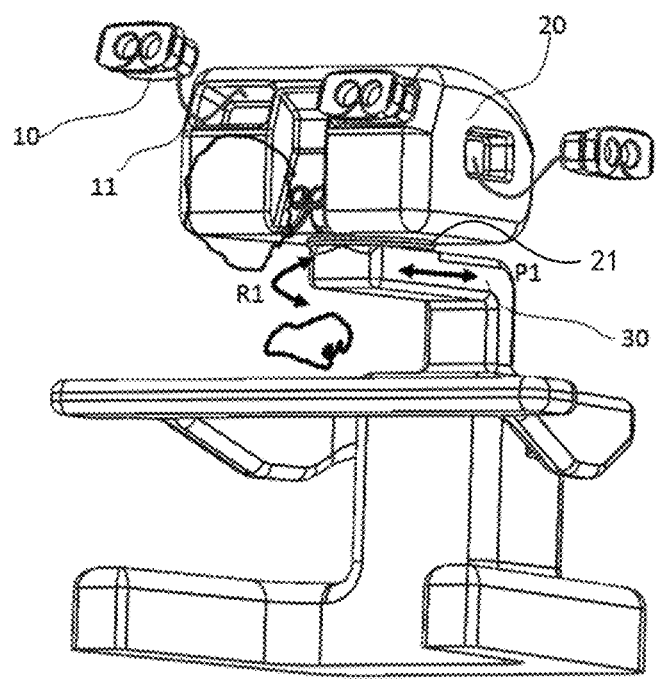
FIG. 1 is a schematic diagram showing an overview of the structure of an imaging system for a surgical robot according to an embodiment of the present invention.
Figure 2:
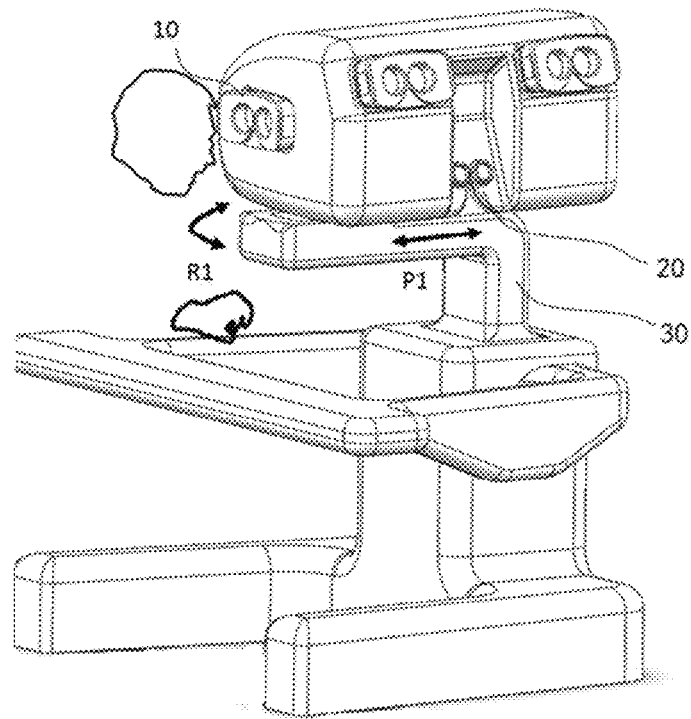
FIG. 2 is a schematic diagram showing the structure of an imaging system for a surgical robot according to an embodiment of the present invention.
Figure 3:
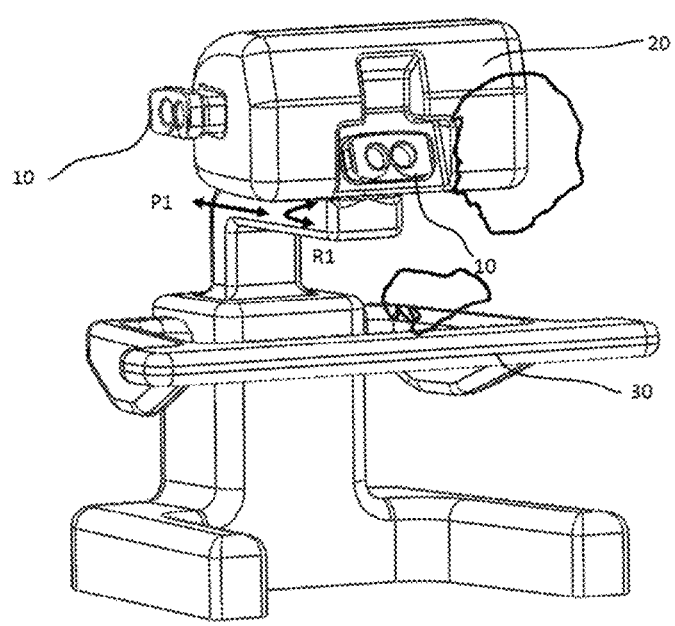
FIG. 3 is a schematic diagram showing the structure of an imaging system for a surgical robot according to another embodiment of the present invention.

FIGS. 1 to 3 schematically illustrate an imaging system for a surgical robot according to an embodiment of the present invention. As illustrated, the imaging system includes a fixed display device 20 for acquiring and displaying image information of a surgical environment. The image information may be displayed as a three-dimensional (3D) stereoscopic image that shows the surgical environment to the operator more intuitively. The imaging system also includes a movable display device 10 that is movably connected to the fixed display device 20, so as to be movable relative. For example, the fixed display device 20 may be provided with a plurality of interfaces for coupling the movable display device 10. As shown in FIG. 1, the movable display device 10 is configured to acquire and display the same image information as is displayed by the fixed display device 20. For example, in an embodiment of the present invention, the movable display device 10 can directly acquire the image information from the fixed display device 20 and display it as a stereoscopic image. The imaging system also includes a console having a support 30 on which the fixed display device 20 is mounted. According to the present invention, the combined use of the movable and fixed display devices provides more options of operation to the operator. The movable display device can be adjusted according to the desired comfort and personal preferences, and provides the operator with an experience of increased operational comfort and reduce the fatigue of the operator. Here, the information of the "surgical environment" may include information of the patient's organ at the treated site such as, for example, a distribution of blood vessels and the type and morphology of the organ, as well as information of a surgical instrument and an endoscope such as, for example, the type and orientation of the surgical instrument.

Preferably, according to the present invention, the fixed display device 20 may include a first display element positioned on the left and a second display element positioned on the right, which are configured to respectively receive image signals from the endoscope, and to display the image signals. The image signals received by the first and second display elements may indicate respective images with binocular disparity therebetween. The fixed display device 20 may further include a first reflector group positioned on the left, a second reflector group positioned on the right, and an image viewer 22 including a first viewing window and a second viewing window. The first viewing window may be positioned left to the second viewing window. The first reflector group may be configured to reflect an image displayed on the first display element to one viewing window of the image viewer 22, and the second reflector group may be configured to reflect an image displayed on the second display element to the other viewing window of the image viewer 22. For example, the first reflector group may be configured to reflect an image displayed on the first display element to the first viewing window, and the second reflector group may be configured to reflect an image displayed on the second display element to the second viewing window. Each viewing window is configured to receive an image from only a respective one of the display elements. As used here, the terms "left" and "right" are intended merely to describe the positional relationships among the display elements, the reflector groups and the viewing windows but not to limit the present invention in any sense.

Preferably, according to the present invention, a plurality of the movable display devices 10 may be provided. With this arrangement, on the one hand, the operator may flexibly choose to use any of the movable display devices 10 as desired, for example, when the operator has moved from one position to another. This increases convenience of operation. On the other hand, the rest movable display device(s) may be used by spectator(s), so as to share images with the operator(s) for surgical training or education. Preferably, each movable display device 10 is movably connected to the fixed display device 20 at the image viewer 22 or on either side of the fixed display device 20.

In order to provide the operator with even greater convenience and a greater space where the operator can move and perform operations in a more comfortable way, according to embodiments of the present invention, the fixed display device 20 may be movably connected, so as to be movable relative, to the support 30 of the console. With this arrangement, the fixed display device 20 and the movable display device(s) 10 thereon can move in an extended range.

In an embodiment of the present invention, the imaging system may further include a turntable structure and a guide track (not shown). The turntable structure may rotate and translate relative to the guide track. Additionally, the guide track may be mounted on the support of the console, and the fixed display device 20 may be connected to the support of the console via the turntable structure 21 and guide track. With this arrangement, the turntable structure 21 imparts a rotational degree of freedom R1 to the fixed display device 20 so that the fixed display device 20 is allowed to be rotate relative to the support 30 of the console, and the guide track connected to the turntable structure 21 imparts a translational degree of freedom P1 to the fixed display device 20 so that the fixed display device 20 is allowed to move along the guide track. In other words, in this embodiment, the fixed display device 20 is connected to the support 30 of the console in a rotatable and translatable manner (with the rotational and translational degrees of freedom R1 and P1).

In some embodiments of the present invention, the movable display device 10 may display the image information as a two-dimensional image. In some other embodiments, the movable display device 10 may display the image information as a 3D image. The latter may be accomplished using any of the following approaches.

In a first approach, the movable display device 10 includes a third display element positioned on the left and a fourth display element positioned on the right. Each of the third and fourth display elements is connected to the same signal source as a respective one of the display elements of the fixed display device 20 by communication means, such as a signal cable 11 or a wireless connection, so that both the display elements can acquire the same image information. Specifically, in order to achieve three-dimensional rendering, the fixed display device 20 generally includes a first display element positioned on the left and a second display element positioned on the right, which are configured to respectively receive image signals from an endoscope, which indicate images with binocular disparity therebetween. When viewing the images displayed on the first and second display elements by seeing through the viewing windows of the image viewer 22 in the fixed display device 20 with the left and right eyes, one will feel as if he/she were watching the real object. The same image information is also provided to the third and fourth display elements of the movable display device 10 through the signal cable 11 or wireless connection. For example, the third display element may receive the same image signal from the same signal source (e.g., a CMOS output signal from the endoscope) as the first display element, and the fourth display element may receive the same image signal from the same signal source (e.g., another CMOS output signal from the endoscope) as the second display element. In this way, a spectator may watch the same stereoscopic image displayed on the two display elements of the movable display device 10 based on binocular visual imaging principle. Likewise, the terms "left" and "right", as used here, are intended merely to describe the positional relationship between the display elements but not to limit the present invention in any way.

Figure 4:
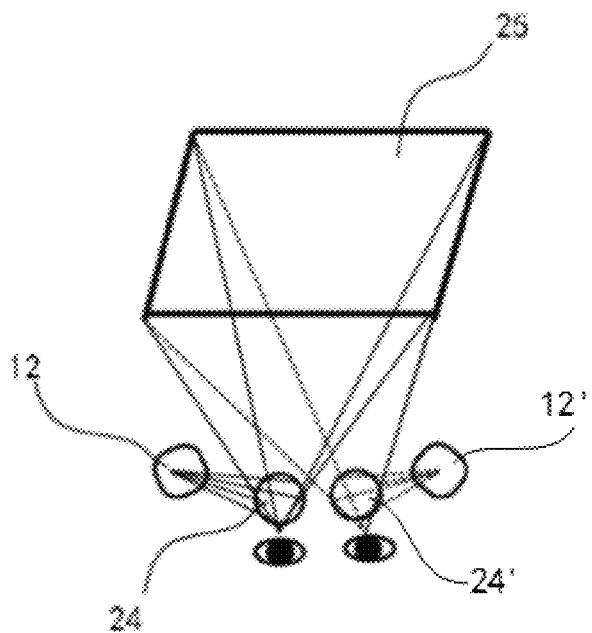
FIG. 4 is a schematic diagram showing an imaging approach employed by a movable display device in an imaging system for a surgical robot according to an embodiment of the present invention.
Figure 5:
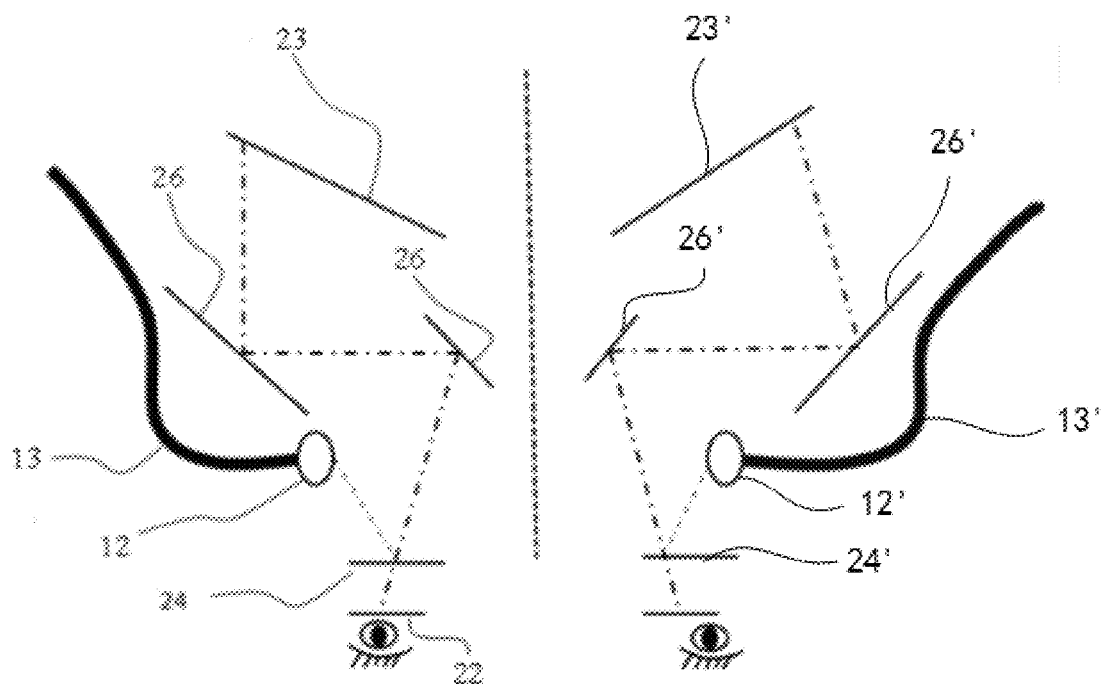
FIG. 5 schematically illustrates how the imaging approach of FIG. 4 works.

In a second approach, as shown in FIGS. 4 and 5, in addition to the third display element positioned on the left and the fourth display element positioned on the right, the movable display device 10 further includes a first light reception element 12 positioned on the left, a second light reception element 12' positioned on the right, a first optical fiber 13 positioned on the left, a second optical fiber 13' positioned on the right, a first image sensing element positioned on the left, a second image sensing element positioned on the right, a first image processing element positioned on the left and a second image processing element positioned on the right. The viewing windows of the image viewer 22 are provided with respective catadioptric lenses, i.e., a first catadioptric lens 24 and a second catadioptric lens 24'. An image displayed on the first display element 23 is reflected by the first reflector group 26, forming a first virtual image. An image displayed on the second display element 23' is reflected by the second reflector group 26', forming a second virtual image, which can be combined with the first virtual image to form a composite virtual image 25. The virtual image 25 is projected onto the respective viewing windows via the catadioptric lenses 24, 24' rather than directly. Further, as shown in FIG. 5, a portion of the reflected image propagates through the first catadioptric lens 24 positioned on the left and reaches the first viewing window of the image viewer 22, while the rest of the reflected light is again reflected by the first catadioptric lens 24 onto the first light reception element 12 of the movable display device 10 and transmitted through the first optical fiber 13 to the first image sensing element (e.g., CMOS or CCD) of the movable display device 10 for photoelectric conversion. The resulting electrical signal is received by the first image processing element, which then applies image enhancement processing such as denoising and sharpening to the received signal. Similarly, a portion of the reflected image propagates through the second catadioptric lens 24 positioned on the right and reaches the second viewing window of the image viewer 22, while the rest of the reflected light is reflected by the second catadioptric lens 24' onto the second light reception element 12' of the movable display device 10 and transmitted through the second optical fiber 13' to the second image sensing element (e.g., CMOS or CCD) of the movable display device 10 for photoelectric conversion. The resulting electrical signal is received by the second image processing element, which then applies image enhancement processing such as denoising and sharpening to the received signal. Finally, the third and fourth display elements of the movable display device 10 display the image resulting from the image signals that have undergone image enhancement processing, so that the operator can view a stereoscopic image using the movable display device 10. This approach allows physical separation of the signals using separate optical paths and ensures complete imaging consistency of the signals.

The present invention also provides a surgical robot including the imaging system as defined above. The surgical robot may further include a master manipulator on the support of the console (as indicated by the hand icon depicted in FIG. 1), a surgical instrument and an image capture device. The master manipulator is configured for manipulation by the operator for adjusting the position and orientation of the surgical instrument. The image capture device may include an endoscope for capturing image information of the surgical environment. The endoscope is communicatively coupled to the fixed display device 20 so as to be able to transmit the captured image information of the surgical environment to the fixed display device 20 for display thereby. Coordinate systems may be defined respectively for the fixed display device 20, the movable display device 10 and the endoscope. The surgical robot may further include a controller configured to match a movement direction and/or an orientational change pattern of the master manipulator in the coordinate system of the movable or fixed display device with a movement direction and/or an orientational change pattern of the surgical instrument in the coordinate system of the endoscope.

In some embodiments, during a surgical procedure, the operator may adjust the position and orientation of the surgical instrument by manipulating the master manipulator while ensuring that the surgical instrument moves just as desired through checking an image of the surgical environment rendered by the display device from image information captured by the endoscope and transmitted to the imaging system. In order to allow intuitive operation of the operator, i.e., operation in accordance with normal human feelings or behavior, a movement direction and an orientational change pattern of the master manipulator relative to the display device (including the movable display device 10 or the fixed display device 20) must be matched with those of the surgical instrument relative to the endoscope. For example, when the operator moves the master manipulator inwardly relative to the fixed display device, i.e., away from his/her eyes, the surgical instrument will move away from the endoscope. As another example, when the operator moves the master manipulator to the right relative to the fixed display device, the surgical instrument will also move to the right relative to the endoscope. To this end, the coordinate systems of the master manipulator, display devices and endoscope must be calibrated during initialization so as to ensure that a movement direction and an orientational change pattern of the surgical instrument relative to the endoscope are matched with those of the master manipulator relative to an intended display device. The master manipulator may be adjusted according to the orientation change of the display device or the endoscope. For example, in a vertically downward orientation of the operator's head on which the movable display device is worn, moving the master manipulator inwardly as seen in the displayed image will lead to the surgical instrument moving away from the endoscope. However, when the operator moves his/her head to a horizontal orientation, the same movement of the master manipulator will cause the surgical instrument to move upward as seen in the displayed image rather than away from the endoscope. Further, a switch between the fixed and movable display devices may be accompanied with a transformation of the coordinate system of the master manipulator from the previous display device to the current display device.

In order to enhance convenience of the operator in performing a surgical procedure based on a displayed image and to provide him/her with a more immersive viewing experience, it is necessary to match a movement direction and an orientational change pattern of the master manipulator relative to the used display device with those of the surgical instrument relative to the endoscope. To this end, it is necessary to preliminarily decide which of the movable and fixed display devices 10, 20 is to be used as a primary display device. The coordinate system of the master manipulator is adapted for any orientation change of the primary display device, and an orientation representation of the master manipulator in the coordinate system of the primary display device is matched with an orientation representation of the surgical instrument in the coordinate system of the endoscope, as described in greater detail below.

The controller may be further configured to receive the operator's choice of the movable or fixed display device as the primary display device. In some embodiments, the movable display device 10 may further include a trigger communicatively connected to the controller, which may trigger when the movable display device 10 is removed from an associated holder in the imaging system. When the controller receives information indicating the triggering of the trigger, the movable display device 10 may be taken as being in an active ON state. The fixed display device 20 may further include an activation switch communicatively connected to the controller. When the controller receives information indicating that the activation switch is triggered, the fixed display device 20 may be taken as being in an active ON state. The surgical robot may further include a primary display device selection button communicatively connected to the controller, which may be configured for the operator to select the movable display device 10 or the fixed display device 20 as the primary display device. Table 1 lists logic values used to determine the primary display device, wherein logic "0" stands for "OFF" and "1" for "ON". As can be seen from the table, if both the movable and fixed display device 10, 20 are in an inactive OFF state, the controller chooses the fixed display device 20 as the primary display device by default. If only the fixed display device 20 is active, the controller also chooses the fixed display device 20 as the primary display device. If only the movable display device 10 is active, the controller chooses the movable display device 10 as the primary display device. If both the movable and fixed display device 10, 20 are active, the operator may determine and select the primary display device manually by interacting with the primary display device selection button. The controller may know (information indicating) the selected primary display device from the operator's manual interaction with the primary display device selection button.

TABLE 1

Logic Values for Determining Primary Display Device

| Logic Value of Movable Display Device | Logic Value of Fixed Display Device | Results of Determination on Primary Display Device |
|---|---|---|
| 0 | 0 | Fixed One |
| 0 | 1 | Fixed One |
| 1 | 0 | Movable One |
| 1 | 1 | By Manual Intervention |

Figure 6:
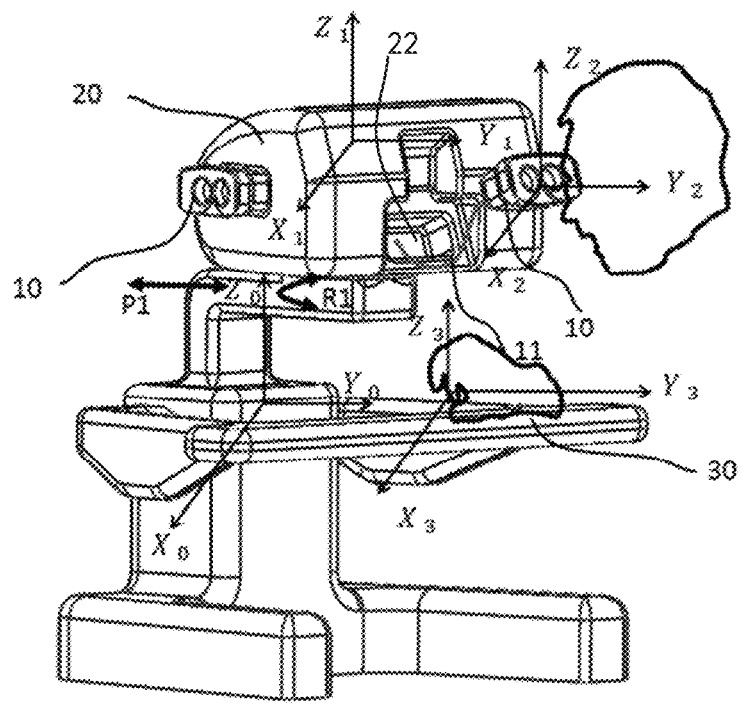
FIG. 6 is a schematic diagram illustrating reference coordinate systems of individual components of a surgical robot according to an embodiment of the present invention.
Figure 7:
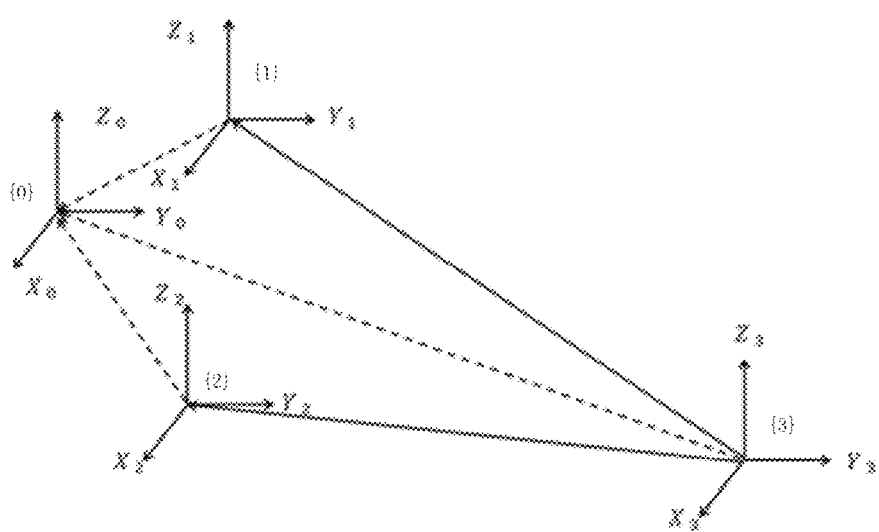
FIG. 7 is a schematic diagram illustrating mappings between the reference coordinate systems of the components of the surgical robot according to an embodiment of the present invention.
Figure 8:
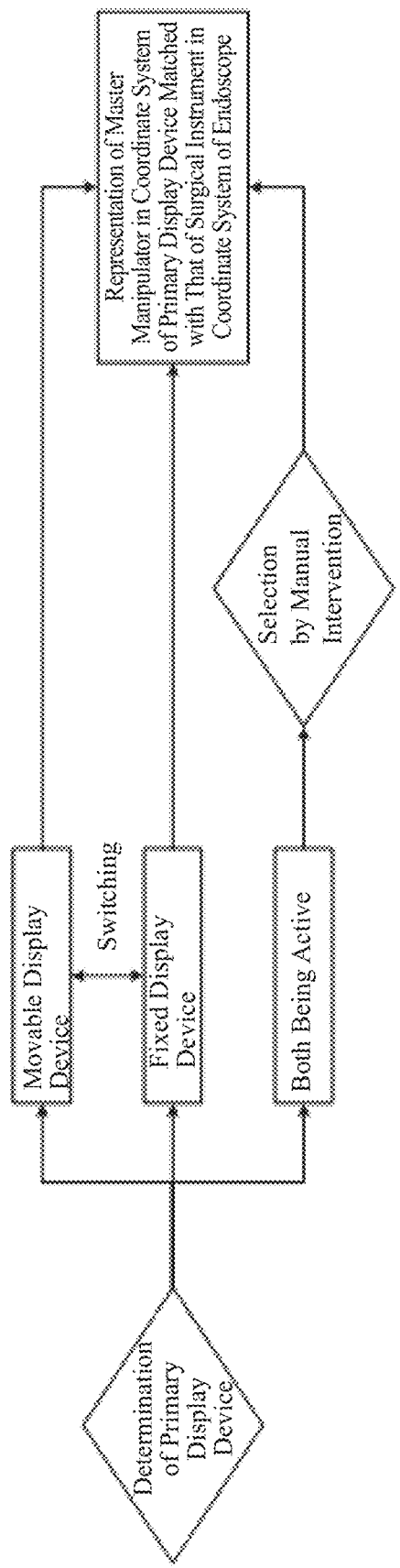
FIG. 8 schematically illustrates a logic flow for determining a primary display device in an imaging system for a surgical robot according to an embodiment of the present invention.

As shown in FIGS. 6 and 7, the coordinate systems of the movable display device 10, the fixed display device 20 and the support 30 of the console may be indicated at {1}, {2} and {0}, respectively. An additional coordinate system {3} may be defined for a grip arranged at one end of the master manipulator. During initialization, ends of the movable display device 10, the fixed display device 20, the support 30 of the console and the master manipulator are calibrated.

In one embodiment, a calibration process may be performed so that the coordinate systems {1} and {3} of the movable display device and the grip rotate in sync with each other relative to the coordinate system {0} of the support of the console, and/or that the coordinate systems {2} and {3} of the fixed display device and the grip rotate in sync with each other relative to the coordinate system {0} of the support of the console. In other words, an orientation in the coordinate system {3} of the grip can be mapped into the coordinate system {2} of the fixed display device according to $^2R_3=E$, and/or an orientation in the coordinate system {3} of the grip can be mapped into the coordinate system {3} of the movable display device according to $^1R_3=E$. The controller may be further configured to make an orientation adjustment to the coordinate system of the grip in the coordinate system of the support of the console based on an orientation change of the coordinate system of the primary display device in the coordinate system of the support of the console.

For example, in case of the movable display device 10 being chosen as the primary display device to display a 3D stereo image to the operator during operation, a gyroscope may be provided on the movable display device 10 to detect an orientation of the coordinate system {1} of the movable display device in the coordinate system {0} of the support of the console. The controller may be communicatively connected to the gyroscope to obtain the orientation of the coordinate system {1} of the movable display device in the coordinate system {0} of the support of the console in real time. Alternatively, the orientation of the coordinate system {1} of the movable display device in the coordinate system {0} of the support of the console may be detected based on the principle of electromagnetic induction using a magnetic field sensor and a horizon sensor both provided in the movable display device 10 that is placed in a magnetic field.

In this case, the controller may be similarly communicatively connected to the magnetic field sensor and the horizon sensor to get the orientation of the coordinate system {1} of the movable display device in the coordinate system {0} of the support of the console in real time. Upon a rotation of the movable display device rotating from a position A to a position B, the controller may derive a rotation matrix $^AR_B$ of the coordinate system {1} of the movable display device from its orientations in the coordinate system {0} of the support of the console at the positions A and B. The controller may further derive an orientation of the coordinate system {3} of the grip at the position B in the coordinate system {0} of the support of the console from both an orientation of the coordinate system {3} of the grip at the position A in the coordinate system {0} of the support of the console and the rotation matrix $^AR_B$ of the coordinate system of the movable display device.

As another example, in case of the fixed display device 20 being chosen as the primary display device to display a three-dimensional stereoscopic image to the operator during operation, if the fixed display device 20 has a rotational degree of freedom R1 relative to the support 30 of the console, a position sensor for detecting an angle of rotation of the fixed display device 20 may be provided on the turntable structure 21 between the fixed display device 20 and the support 30 of the console. Moreover, the controller may be communicatively connected to the position sensor to acquire an orientation of the coordinate system {2} of the fixed display device 20 in real time. When the fixed display device rotates from a position C to a position D, the controller may derive a rotation matrix $^CR_D$ of the coordinate system of the fixed display device from its orientations in the coordinate system {0} of the support of the console at the positions C and D. The controller may further derive an orientation of the coordinate system {3} of the grip at the position D in the coordinate system {0} of the support of the console from both an orientation of the coordinate system {3} of the grip at the position C in the coordinate system {0} of the support of the console and the rotation matrix $^CR_D$ of the coordinate system of the fixed display device.

When the primary display device switches from the movable display device 10 to the fixed display device 20, the controller may derive a movable-to-fixed rotation matrix R from both orientations of the coordinate system {2} of the movable display device and the coordinate system {1} of the fixed display device in the coordinate system {0} of the support of the console; and make an orientation adjustment to the coordinate system {3} of the grip in the support of the coordinate system {0} of the support of the console based on the movable-to-fixed rotation matrix R. On the contrary, when the primary display device switches from the fixed display device 20 to the movable display device 10, the controller may derive a fixed-to-movable rotation matrix R' from both orientations of the coordinate system {2} of the movable display device and the coordinate system {1} of the fixed display device in the coordinate system {0} of the support of the console and make an orientation adjustment to the coordinate system {3} of the grip in the coordinate system {0} of the support of the console based on the fixed-to-movable rotation matrix R'.

In addition, master-slave mapping and synchronization may be achieved by matching an orientation representation of the surgical instrument in the coordinate system of the endoscope with an orientation representation of the master manipulator in the coordinate system of the active display device. To this end, in addition to making an orientation adjustment to the coordinate system of the grip in the coordinate system of the support of the console based on an orientation change of the coordinate system of the primary display device in the coordinate system of the support of the console, the controller may be further configured to make an orientation adjustment to the master manipulator based on an orientation representation of the surgical instrument in the coordinate system of the endoscope so as to match an orientation representation of the master manipulator in the coordinate system of the primary display device with the orientation representation of the surgical instrument in the coordinate system of the endoscope. Coordinate systems {4} and {5} may be further defined for the surgical instrument and the endoscope. During initialization, the coordinate systems for the movable display device 10, the fixed display device 20, the master manipulator, the endoscope and the surgical instrument may be calibrated, so that an orientation in the coordinate system {3} of the grip is mapped into the coordinate system {2} of the movable display device or into the coordinate system {1} of the fixed display device in the same way as a corresponding orientation in the coordinate system {4} of the surgical instrument is mapped into the coordinate system {5} of the endoscope. In this way, although the orientation of the coordinate system {3} of the grip in the coordinate system {0} of the support of the console will always change with the orientation of the coordinate system {2} of the movable display device in the coordinate system {0} of the support of the console, any change in the orientation of the coordinate system {2} of the movable display device will lead to a mismatch between the orientation representation of the master manipulator in the newly-oriented coordinate system {2} of the movable display device and the orientation representation of the surgical instrument in the coordinate system {5} of the endoscope. Therefore, in addition to the orientation adjustment made to the coordinate system {3} of the grip, it is also necessary for the controller to utilize a kinematic model to adjust different joints of the master manipulator, based on the orientation representation of the surgical instrument in the coordinate system {5} of the endoscope to match the orientation representation of the master manipulator in the coordinate system {2} of the movable display device in the new orientation with the orientation representation of the surgical instrument in the coordinate system {5} of the endoscope. In case of the fixed display device 20 having a rotational degree of freedom R1 relative to the support 30 of the console, i.e., with adjustability in its orientation, the master manipulator will be adjusted in a similar manner to match an orientation representation of the master manipulator in the coordinate system {1} of the fixed display device that has experienced any change with the orientation representation of the surgical instrument in the coordinate system {5} of the endoscope.

With the above-described mappings and transformations, no matter which of the display devices is chosen as the primary display device, coordinate systems can be correctly mapped and transformed between the primary display device and the master manipulator, resulting in a match of the orientations as observed in the image and of the manipulated robotic arm system with the coordinate relationship between the surgical instrument and the endoscope. This enables correct motion detection and control.

The image capture device may further include: actuation elements for adjust the orientation of the endoscope; and orientation detection elements for detecting the endoscope's orientation. The controller may be communicatively connected to both the actuation elements and the orientation detection elements and configured to control the actuation elements to make an orientation adjustment based on the orientation of the movable display device and the current orientation of the endoscope, and thus result in a match between the orientations of the endoscope and the movable display device.

The image capture device may include an endoscope holding arm, on which the endoscope is held, and which may include a plurality of joints. The orientation detection elements may be configured to detect angles of rotation of the joints, and the actuation elements may be connected to the joints and configured to drive them to rotate. The controller may determine the current orientation of the endoscope from measurements of the orientation detection element using a kinematic model and determine amounts of rotation for the respective joints of the endoscope holding arm from the orientation of the movable display device (corresponding to a target orientation for the endoscope). Subsequently, the controller may control the actuation elements to drive the joints to rotate, thus resulting in a match between the orientations of the endoscope and the movable display device. Reference can be made to Chinese Patent Publication No. CN106333715A for more details in this regard, which is incorporated herein by reference in its entirety as part of this application.

The operator may vary the orientation of the movable display device to cause the endoscope to move as desired in a controlled manner. This enables a surgical procedure to be conducted more smoothly with increased efficiency. On the other hand, any change in the endoscope's orientation is accompanied by an opposite change in the orientation of the surgical instrument. In order to achieve a match between an orientation representation of the master manipulator in the coordinate system {2} of the movable display device that has experienced an orientation change and an orientation representation of the surgical instrument in the coordinate system {5} of the endoscope that has experienced a responsive orientation change, in addition to adjusting the master manipulator so that an orientation representation of the master manipulator in the newly-oriented coordinate system {2} of the movable display device is matched with an orientation representation of the surgical instrument in the coordinate system {5} of the endoscope in the previous orientation, it is also necessary to further adjust the master manipulator so that a match is also achieved between the orientation representation of the master manipulator in the newly-oriented coordinate system {2} of the movable display device and an orientation representation of the surgical instrument in the coordinate system {5} of the endoscope with the new orientation. Accordingly, the controller may be further configured to adjust the orientations of the coordinate system {3} of the grip and of the endoscope based an orientation change of the coordinate system {2} of the movable display device in the coordinate system {0} of the support of the console and thus obtain an adjusted coordinate system of the endoscope. Additionally, the controller may be configured to adjust the orientation of the master manipulator based an orientation representation of the surgical instrument in the adjusted coordinate system of the endoscope so as to match an orientation representation of the master manipulator in the coordinate system {2} of the movable display device with the orientation representation of the surgical instrument in the coordinate system {5} of the endoscope.

Further, in order to avoid the endoscope from varying in position or orientation with the movable display device in an undesirable way, the surgical robot may further include a follow switch communicatively connected to the controller, which may be configured to enable or disable the controller to control the endoscope to vary in position or orientation with the movable display device.

The present invention is not limited to any particular type of the controller because it may be implemented as hardware that performs logic operations, such as a single-chip microcomputer, a microprocessor, a programmable logic controller (PLC) or a field-programmable gate array (FPGA), or software programs, functional modules, functions, object libraries or dynamic-link libraries, which provide the above-mentioned functions on the basis of hardware, or a combination of both. On the basis of the teachings disclosed herein, a person of ordinary skill in the art would know how to specifically implement communications between the controller and other components.

Further, the present invention is not limited to any particular type of the display devices. For example, cathode ray tube (CRT), plasma display panel (PDP), liquid crystal display (LCD), light-emitting diode (e.g., LED, mini-LED, AMOLED or OLED) devices are all possible. A person of ordinary skill in the art can select a suitable type according to the intended use environment and the requirements of the imaging system's functions.

In summary, the present invention provides an imaging system for a surgical robot, which combines a movable display device with a fixed display device, providing more options of operation to an operator. The movable display device can be adjusted according to the desired comfort and personal preferences to provide the operator with an experience of increased operational comfort and reduce the fatigue of the operator.

Additionally, a plurality of the movable display devices may be included, and image information can be synchronized between the individual movable display devices and between each movable display device and the fixed display device. This enables the operator and assisting staff to watch the progress of a surgical procedure with the same view, increasing safety of the procedure. When used in surgical training and education applications, the participation of an operator and several trainees is allowed, ensuring enhanced reality of the training and improved training efficiency.

The present invention also provides a surgical robot, which incorporates the imaging system and preferably matches a movement direction and/or orientational change pattern of a master manipulator in a coordinate system of a primary display device with a movement direction and/or orientational change pattern of a surgical instrument in a coordinate system of an endoscope. The surgical robot provides an operator with an immersive experience, correct motion detection and control, and higher control accuracy in performing image information based operations.

In addition, the surgical robot allows the orientation of an endoscope, a laparoscope or a similar instrument in an image capture device to change with the orientation of the movable display device. In this way, the endoscope, laparoscope or instrument moves exactly as desired by the operator, enabling a surgical procedure to be conducted more smoothly with increased efficiency.

The foregoing description presents merely a few preferred embodiments of the present invention and is not intended to limit the scope thereof in any sense. Any and all changes and modifications made by those of ordinary skill in the art based on the above teachings also fall within the scope as defined in the appended claims.

What is claimed is:

1. A surgical robot, comprising:
a fixed display device configured to acquire and display image information about a surgical environment;
a movable display device, which is coupled to the fixed display device, and is movable relative to the fixed display device, the movable display device configured to acquire and display the image information that is displayed by the fixed display device;
a console having a support on which the fixed display device is mounted;
a controller, configured to determine which one of the movable display device and the fixed display device is selected as a primary display device according to a selection from an operator;
an image capture device, comprising an endoscope configured to capture the image information about the surgical environment, the fixed display device is communicatively connected to the endoscope, so as to acquire the image information about the surgical environment, and
a master manipulator, on the support of the console, wherein the master manipulator is configured to control position and orientation adjustment to a surgical instrument,
wherein coordinate systems are defined respectively for the fixed display device, the movable display device and the endoscope,
wherein the controller is further configured to match a movement direction and/or an orientational change pattern of the master manipulator in the coordinate system of the primary display device with a movement direction and/or an orientational change pattern of the surgical instrument in the coordinate system of the endoscope;
wherein coordinate systems are defined respectively for a grip of the master manipulator and for the support of the console;
wherein the controller is further configured to make an orientation adjustment to the coordinate system of the grip in the coordinate system of the support of the console based on an orientation change of the coordinate system of the primary display device in the coordinate system of the support of the console, and to make an orientation adjustment to the master manipulator based on an orientation representation of the surgical instrument in the coordinate system of the endoscope, so as to match an orientation representation of the master manipulator in the coordinate system of the primary display device, with the orientation representation of the surgical instrument in the coordinate system of the endoscope; or
wherein when the primary display device is switched from the movable display device to the fixed display device, the controller determines a movable-to-fixed rotation matrix from an orientation of the coordinate system of the movable display device in the coordinate system of the support of the console and an orientation of the coordinate system of the fixed display device in the coordinate system of the support of the console, adjusts an orientation of the coordinate system of the grip in the coordinate system of the support of the console based on the movable-to-fixed rotation matrix, and makes an orientation adjustment to the master manipulator based on the an orientation representation of the surgical instrument in the coordinate system of the endoscope so as to match an orientation representation of the master manipulator in the coordinate system of the fixed display device with the orientation representation of the surgical instrument in the coordinate system of the endoscope; or
wherein when the primary display device is switched from the fixed display device to the movable display device, the controller determines a fixed-to-movable rotation matrix from an orientation of the coordinate system of the movable display device in the coordinate system of the support of the console and an orientation of the coordinate system of the fixed display device in the coordinate system of the support of the console, adjusts an orientation of the coordinate system of the grip in the coordinate system of the support of the console based on the fixed-to-movable rotation matrix, and makes an orientation adjustment to the master manipulator based on the an orientation representation of the surgical instrument in the coordinate system of the endoscope so as to match an orientation representation of the master manipulator in the coordinate system of the movable display device with the orientation representation of the surgical instrument in the coordinate system of the endoscope.

2. The surgical robot of claim 1, wherein the movable display device is provided with a gyroscope configured to detect an orientation of the coordinate system of the movable display device in coordinate system of the support of the console, and the controller is communicatively connected to the gyroscope so as to determine an orientation change of the coordinate system of the movable display device in the coordinate system of the support of the console, or
wherein the movable display device is provided with a magnetic field sensor and a horizon sensor, which are configured to detect an orientation of the coordinate system of the movable display device in the coordinate system of the support of the console, and the controller is communicatively connected to both the magnetic field sensor and the horizon sensor so as to determine an orientation change of the coordinate system of the movable display device in the coordinate system of the support of the console based on a principle of electromagnetic induction.

3. The surgical robot of claim 1, wherein the fixed display device is movably mounted on the support of the console via a turntable structure so as to be movable relative to the support of the console, and wherein the turntable structure is provided thereon with a position sensor configured to sense an angle of rotation of the fixed display device, and the position sensor is communicatively connected to the controller so that the controller is able to determine an orientation change of the coordinate system of the fixed display device in the coordinate system of the support of the console using both the position sensor and a kinematic model.

4. The surgical robot of claim 1, wherein the image capture device further comprises: an actuation element configured to adjust an orientation of the endoscope, and an orientation detection element configured to detect the orientation of the endoscope, and wherein
the controller is communicatively connected to both the actuation element and the orientation detection element, and is configured to control the actuation element, based on an orientation of the movable display device and a current orientation of the endoscope, to drive the endoscope so as to achieve a match between the orientations of the endoscope and the movable display device.

5. The surgical robot of claim 4, wherein the image capture device further comprises an endoscope holding arm by which the endoscope is held,
wherein the endoscope holding arm comprises a plurality of joints, the orientation detection element is connected to the joints to detect angles of rotation of the joints, and the actuation element is connected to the joints to drive the joints to move, and wherein
the controller is configured to determine a current orientation of the endoscope from measurements of the orientation detection element using a kinematic model; determine amounts of rotation for the joints of the endoscope holding arm from the orientation of the movable display device, and control the actuation element to drive the joints to rotate to result in a match between the orientations of the endoscope and the movable display device.

6. The surgical robot of claim 5, wherein the image capture device further comprises a follow switch communicatively connected to the controller, wherein the follow switch is configured to enable or disable the controller to control the endoscope to vary in position or orientation with the movable display device.

7. The surgical robot of claim 4, wherein
the controller is further configured to adjust an orientation of the coordinate system of the grip and the orientation of the endoscope based on an orientation change of the coordinate system of the movable display device in the coordinate system of the support of the console and to adjust an orientation of the master manipulator based on an orientation representation of the surgical instrument in the adjusted coordinate system of the endoscope so as to achieve a match between an orientation representation of the master manipulator in the coordinate system of the movable display device and an orientation representation of the surgical instrument in the adjusted coordinate system of the endoscope.

8. The surgical robot of claim 1, wherein the fixed display device is movably connected to the support of the console so that the fixed display device is movable relative to the support of the console.

9. The surgical robot of claim 8, further comprising a guide track mounted on the support of the console, and a turntable structure configured to be moved rotatably and/or translationally along the guide track, wherein the fixed display device is connected to the support of the console via the turntable structure and guide track.

10. The surgical robot of claim 1, wherein the fixed display device comprises a first display element, a second display element, a first reflector group, a second reflector group, and an image viewer having a first viewing window and a second viewing window, wherein the first display element and the second display element are configured to respectively receive image signals indicative of respective images with binocular disparity therebetween and display the images, the first reflector group is configured to reflect the image displayed on the first display element to the first viewing window of the image viewer, the second reflector group is configured to reflect the image displayed on the second display element to the second viewing window of the image viewer, and each of the first viewing window and the second viewing window is configured to receive the image displayed on one of the first display element and the second display element.

11. The surgical robot of claim 10, wherein the movable display device is movably connected to the image viewer of the fixed display device, or on either side of the fixed display device.

12. The surgical robot of claim 10, wherein the movable display device comprises a third display element and a fourth display element, wherein each of the third display element and the fourth display element is communicatively connected to a signal source for a respective one of the display elements of the fixed display device so as to able to acquire an image signal same as the image signal received by the respective display element.

13. The surgical robot of claim 10, wherein:
the movable display device comprises a third display element, a fourth display element, a first light reception element, a second light reception element, a first optical fiber, a second optical fiber, a first image sensing element, a second image sensing element, a first image processing element and a second image processing element;
wherein a first catadioptric lens is mounted to the first viewing window of the image viewer in the fixed display device, and configured to allow part of light of an image displayed on the first display element, which has been reflected by the first reflector group, to pass through the first catadioptric lens onto the first viewing window and to reflect rest of the light onto the first light reception element, and the reflected part of the light is then transmitted through the first optical fiber to the first image sensing element and photoelectrically converted by the first image sensing element into an electrical signal which is received by the first image processing element, undergoes image enhancement processing therein, and the third display element is configured to display an image resulting from the image enhancement processing in the first image processing element; and
wherein a second catadioptric lens is mounted to the second viewing window of the image viewer in the fixed display device, and configured to allow part of light of an image displayed on the second display element, which has been reflected by the second reflector group, to pass through the second catadioptric lens onto the second viewing window and to reflect the rest of the light onto the second light reception element, and the reflected part of the light is then transmitted through the second optical fiber to the second image sensing element and photoelectrically converted thereby into a further electrical signal which is received by the second image processing element, undergoes image enhancement processing therein, and the fourth display element is configured to display a further image resulting from the image enhancement processing in the second image processing element.

\* \* \* \* \*